US009898789B2

(12) United States Patent
Ram et al.

(10) Patent No.: US 9,898,789 B2
(45) Date of Patent: Feb. 20, 2018

(54) METHOD AND A SYSTEM FOR PROVIDING HOSTED SERVICES BASED ON A GENERALIZED MODEL OF A HEALTH/WELLNESS PROGRAM

(71) Applicant: Palo Alto Research Center Incorporated, Palo Alto, CA (US)

(72) Inventors: Ashwin Ram, Palo Alto, CA (US); Gregory Michael Youngblood, San Jose, CA (US); Peter L. Pirolli, San Francisco, CA (US); Lester D. Nelson, Santa Clara, CA (US); Jesse Vig, Palo Alto, CA (US); Shane P. Ahern, Foster City, CA (US); Jonathan Rubin, Palo Alto, CA (US); Christina Pavlopoulou, Menlo Park, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 523 days.

(21) Appl. No.: 13/863,396

(22) Filed: Apr. 16, 2013

(65) Prior Publication Data

US 2014/0310013 A1    Oct. 16, 2014

(51) Int. Cl.

| G06Q 10/00 | (2012.01) |
|---|---|
| G06Q 50/00 | (2012.01) |
| G06Q 50/22 | (2018.01) |
| G06Q 10/10 | (2012.01) |
| G06F 9/44 | (2018.01) |
| G06Q 50/24 | (2012.01) |

(52) U.S. Cl.
CPC .............. *G06Q 50/22* (2013.01); *G06F 8/30* (2013.01); *G06Q 10/10* (2013.01); *G06Q 50/24* (2013.01)

(58) Field of Classification Search
CPC ........... G06Q 50/22; G06Q 50/24; G06F 8/30
See application file for complete search history.

(56) References Cited

U.S. PATENT DOCUMENTS

| 2005/0113650 A1* | 5/2005 | Pacione | A61B 5/411 600/300 |
|---|---|---|---|
| 2007/0261024 A1* | 11/2007 | Kodosky | G06F 8/10 717/106 |
| 2012/0303377 A1* | 11/2012 | York | G06Q 50/22 705/2 |
| 2013/0090749 A1* | 4/2013 | Oswald | A63B 24/0062 700/91 |
| 2013/0138450 A1* | 5/2013 | Vigneux | G06Q 10/00 705/2 |
| 2014/0156308 A1* | 6/2014 | Ohnemus | G06F 19/3418 705/3 |
| 2014/0278449 A1* | 9/2014 | Kharraz Tavakol | G06F 19/345 705/2 |

* cited by examiner

*Primary Examiner* — Christopher L Gilligan
(74) *Attorney, Agent, or Firm* — Shun Yao; Park, Vaughan, Fleming & Dowler LLP

(57) ABSTRACT

One embodiment of the present invention provides a system for creating a health/wellness program on a generic health/wellness platform. During operation, the system receives, at the generic health/wellness platform, a set of definitions for the health/wellness program, constructs a program model for the health/wellness program, generates a program instance to be executed on the generic health/wellness platform, and associates the program instance to a number of health/wellness modules provided by the health/wellness platform.

16 Claims, 11 Drawing Sheets

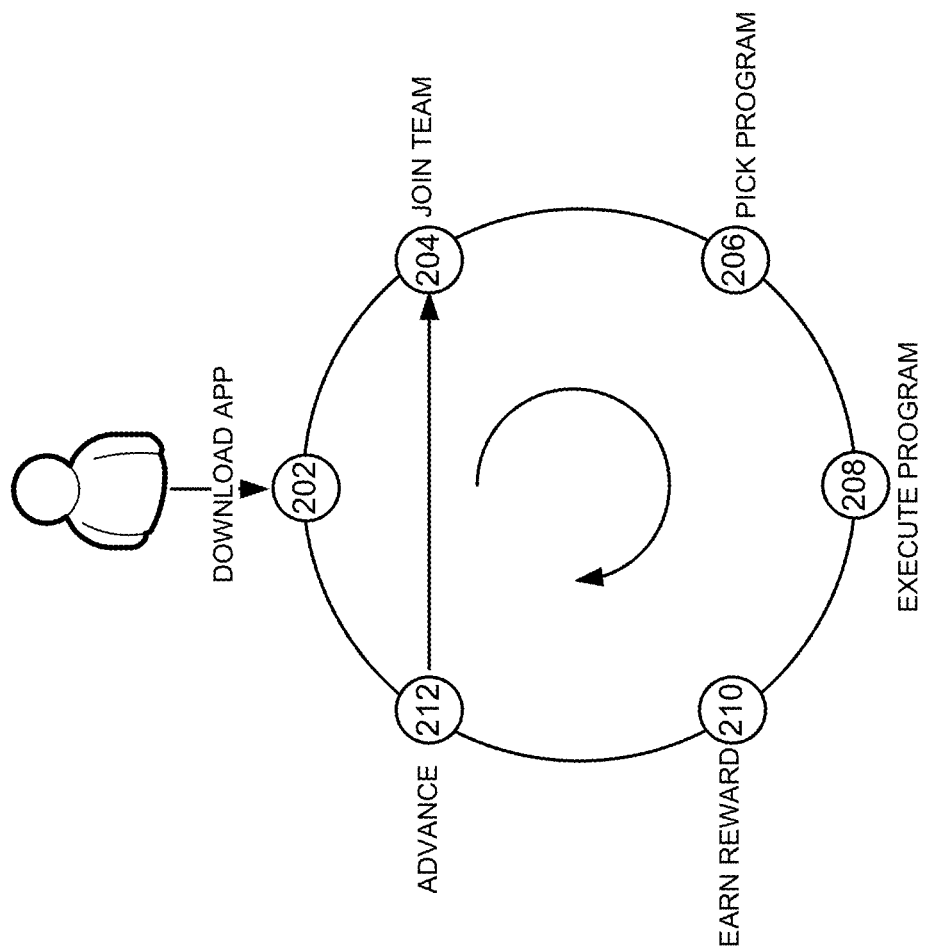

```xml
<?xml version="1.0" encoding="utf-8"?>
<aiml version="1.0" >
<category>
    <pattern>*</pattern>
    <template>Thank you for checking out Nudge. Do you think you are eating as healthy and being as physically active as you should be?</template>
</category>

<category>
<pattern>YES</pattern>
<that>* AS YOU SHOULD BE</that>
<template>That's great. ~dialogue ER_CheckBM</template>
</category>

<category>
<pattern>NO</pattern>
<that>* AS YOU SHOULD BE</that>
<template>This application is meant to help you with that improvement. We do this by letting you set goals that you feel you can do now that will help.
~dialogue ER_AppTry</template>
</category>

<category>
<pattern>MAYBE</pattern>
<that>* AS YOU SHOULD BE</that>
<template>This application is meant to help you with such improvement. We do this by letting you set goals that you feel you can do now that will help. If you are not sure about improving your level of activity or healthy eating, using the application might help you understand your needs better. ~dialogue ER_AppTry
</template>
</category>

<category>
<pattern>*</pattern>
<that>* AS YOU SHOULD BE</that>
<template>Was that Yes or No about being as healthy as you should be?</template>
</category>

</aiml>
```

Links to another ALML Dialog Specification

FIG. 3C

METHOD AND A SYSTEM FOR PROVIDING HOSTED SERVICES BASED ON A GENERALIZED MODEL OF A HEALTH/WELLNESS PROGRAM

BACKGROUND

Field

This disclosure is generally related to a system for promoting health and/or wellness. More specifically, this disclosure is related to a general platform that allows any provider to define a health/wellness program as a hosted service.

Related Art

Skyrocketing healthcare costs have prompted everyone, including government, private corporations, insurance companies, etc., to search for solutions that can lower these costs. Studies have shown that 50% of healthcare costs are attributed to lifestyle choices and can be mitigated by adoption of healthy lifestyles. For example, some common diseases, such as high blood pressure and diabetes, may be prevented or controlled by changing lifestyles. Various types of programs can be used to promote healthy lifestyles or to improve general personal health, including diet plans, exercise plans, and mobile apps that track health-related data in a person's daily life.

However, most of these programs suffer from key limitations that include creation cost, selection difficulties, and lack of ways to improve user stickiness. First, a provider that wishes to offer its customers or employees programs that promote health and/or wellness may find that the cost associated with creating and implementing particular programs that are customized to suit the needs of a particular demographic group can be high. For example, it may cost millions to develop and test a customized app for a single lifestyle intervention scheme, such as an app that can help people to control irregular blood pressure. Second, a consumer may be overwhelmed by a large array of programs that are available and find it difficult to select a program that can best suit his needs. Moreover, the effectiveness of these health/wellness programs depends on how well their users stick with the program. Most programs lack mechanisms that can effectively enhance the likelihood of the user sticking with the program. In general, based on most studies, over 50% of health/wellness program users drop out of the program after a mere three-and-a-half weeks.

SUMMARY

One embodiment of the present invention provides a system for creating a health/wellness program on a generic health/wellness platform. During operation, the system receives, at the generic health/wellness platform, a set of definitions for the health/wellness program, constructs a program model for the health/wellness program, generates a program instance to be executed on the generic health/wellness platform, and associates the program instance to a number of health/wellness modules provided by the health/wellness platform.

In a variation on this embodiment, the health/wellness modules include one or more of: a social conversation engine, a contextual data acquisition module, a recommendation engine, a coaching agent, and a dialogue agent.

In a further variation, the recommendation engine is configured to provide recommendations to a user of the health/wellness program based at least on user context obtained by the contextual data acquisition module.

In a further variation, the recommendation engine is configured to recommend to a user one or more of: a health/wellness program hosted by the health/wellness generic platform, a challenge associated with the recommended health/wellness program, a team to join for participating the recommended health/wellness program, and a challenge to the team.

In a further variation, the coaching agent is configured to: measure a probability that a user of the health/wellness program will achieve a behavior goal defined by the health/wellness program, and deliver interventions in response to the measured probability being less than a predetermined threshold.

In a further variation, the interventions are delivered to the user or a teammate of the user.

In a further variation, the dialog agent maintains at least one persistent Artificial Intelligence Modeling Language (AIML) dialog instance.

One embodiment of the present invention provides a system for facilitating a user in participating in a health/wellness program. During operation, the system collects, by a computing device, context information associated with the user; recommends, to the user, a health/wellness program; recommends a team for the user to join when participating in the recommended health/wellness program; monitors the user's progress. Furthermore, the system facilitates goal substitutions by using appropriate, personalized equivalence calculations, and delivers interventions to the user, thereby assisting the user in sticking to the health/wellness program.

In a variation on this embodiment, the system recommends a challenge within the health/wellness program.

In a variation on this embodiment, the context information associated with the user includes one or more of: demographic data; personality data; social network data, and textual data associated with the user.

In a variation on this embodiment, monitoring the user's progress involves determining a probability that the user will achieve a behavior goal defined by the health/wellness program.

In a variation on this embodiment, delivering the interventions involves an Artificial Intelligence Modeling Language (AIML) dialog instance.

In a variation on this embodiment, recommending the team for the user to join involves one or more of: calculating a similarity measure between the user and the team, calculating an affinity measure between the user and members of the team, and calculating dynamics associated with the team.

BRIEF DESCRIPTION OF THE FIGURES

FIG. 2 presents a diagram illustrating the system flow as perceived by the users, in accordance with an embodiment of the present invention.

FIG. 3C presents a diagram illustrating an exemplary AIML dialog specification for top of the dialog tree shown in FIG. 3B.

In the figures, like reference numerals refer to the same figure elements.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Overview

Embodiments of the present invention provide a novel hosted platform that allows any health/wellness program provider to implement a heath/wellness program as a hosted service and offer the health/wellness program to the desired population via an app. In addition, the platform provides a user guidance mechanism that allows users to select, participate either by themselves or in a team, and customize through a method of curation by a social community a health/wellness program. The formation of the social teams and the personalized coaching agent provided by the hosted platform increase the user stickiness. More specifically, the platform includes a meta-system for constructing and supporting individual program instances, specific services and models that comprise individual program instances, means for translating program definitions into individual program instances, user components (including user modeling, interaction elements, and recommendation services needed to enable users to make maximum use of the program instances), and social components (including social modeling, interaction elements, and recommendation services that enable groups of users to make maximum use of the program instances).

In the disclosure, the term "app" refers to a computer software module that is designed to help its users to perform specific tasks. An app can be installed on various computing devices, including but not limited to: a mainframe computer, a personal computer (PC), and various portable computing devices, such as a laptop computer, a tablet computer, and a smartphone. Furthermore, there term "health/wellness" refers to a platform, program, or application related to the health and/or wellness of a user. Note that "health" and "wellness" are not used in a mutually exclusive manner herein. The term "challenge" may refer to one or more tasks as a specific type or part of a health/wellness program. Although the present disclosure uses iPhone and iOS as examples, embodiments of the present invention are not limited to any specific type of phones. Embodiments of the present invention can be implemented on different smartphone platforms, such as Android phones, or based on SMS/text messaging, or on Web-based platforms.

System Architecture

Figure 1A:
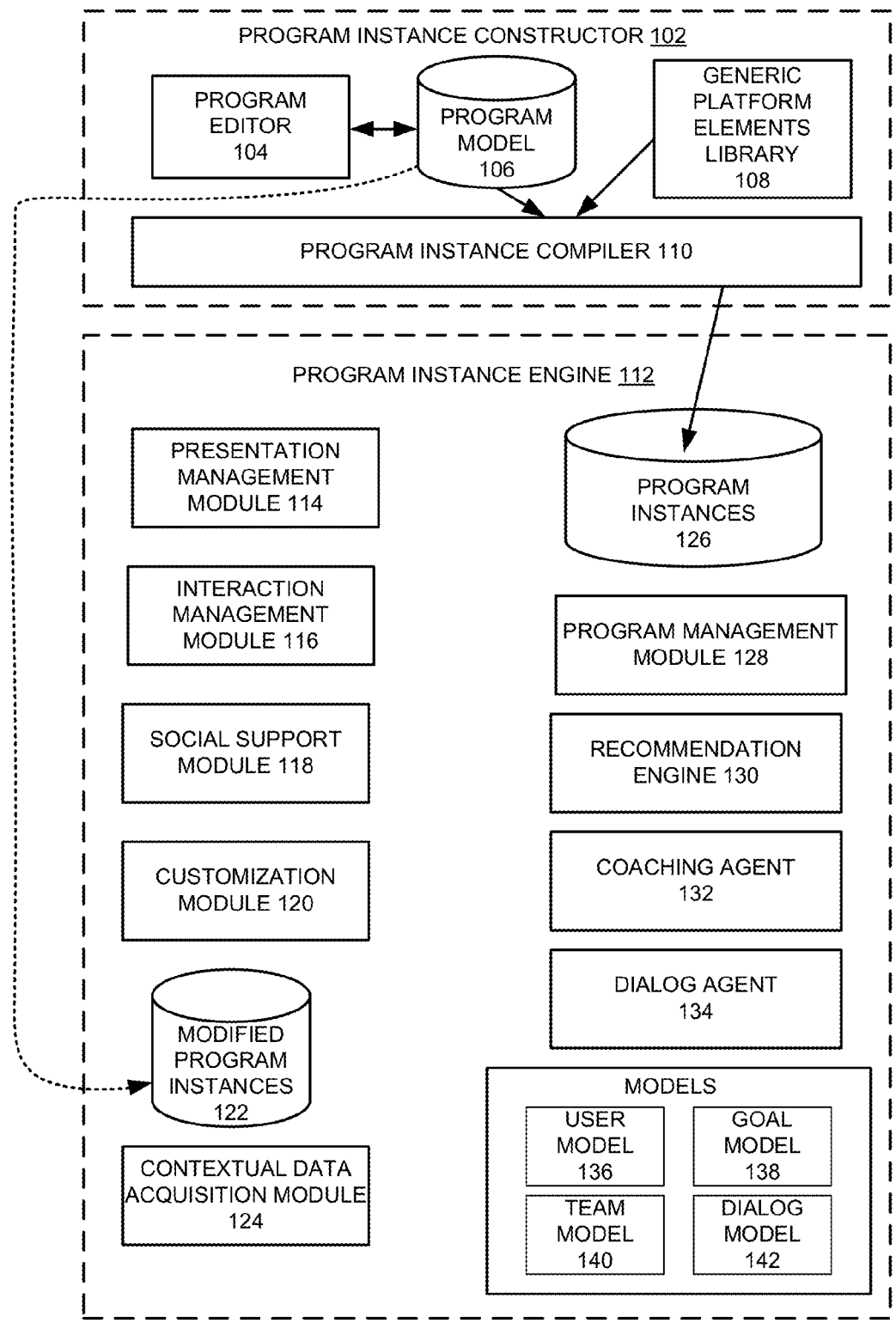
FIG. 1A presents a diagram illustrating an exemplary generic health/wellness platform, in accordance with an embodiment of the present invention.

FIG. 1A presents a diagram illustrating an exemplary generic health/wellness platform, in accordance with an embodiment of the present invention. Generic health/wellness platform 100 includes a program instance constructor 102 and a program instance engine 112.

Program instance constructor 102 facilitates implementation of the health/wellness program and provides administrative support for the health/wellness program. In the example shown in FIG. 1A, program instance constructor 102 includes a program editor 104, a program model database 106, a generic platform elements library 108, and a program instance compiler 110. More specifically, program instance constructor 102 allows any provider to define a health/wellness program as a hosted service on generic health/wellness platform 100.

During operation, program editor 104 interfaces with the creator of a health/wellness program and provides the interaction elements by which the program creator may specify a number of program elements, including but not limited to: program activities and dependencies; activity ranges and constraints (including temporal, spatial, and physical ranges and constraints); relevant information and motivational content (such as an instruction manual); incentives and reward structures (which include gamification elements, such as badges, points, leaderboard, etc.); various types of information associated with the health/wellness program that are informative, instructional, demonstrative, or other (including but not limited to: images, audio, video, interactive elements such as mini-games, and media for the sensory impaired, such as Braille, forced feedback, and unique audio tones); and associated references to external resources that can augment data informational elements in the system.

The program editing performed by program editor 104 results in a program model stored in program model database 106. The program model quantifies the interaction elements specified by the program creator and may be represented in a number of ways, including but not limited to: a graph model; a database (such as a relational, a distributed, or a rule-based database); a repository (a data structure, such as XML or other structured or semi-structured data type); flat files; a software module; and physical documents of the program details (such as books, eBooks, brochures, etc.).

Generic platform elements library 108 includes a number of generic platform elements that can be used by program instance compiler 110 to generate components needed to execute an individual health/wellness program instance. The generic platform elements include but are not limited to: user and social software administration frameworks, recommendation engines, conversational dialog managers, mobile application components and services, communication and database services, client/server elements and supporting communication protocols, planners and schedulers, experience managers, coaching agents, visual display information including data analytics, etc.

While compiling a program instance for a particular health/wellness program, program instance compiler 110 takes the program model stored in program model database 106 and generates the components needed to execute an individual program instance on generic platform 100 based on the available generic platform elements included in generic platform elements library 108. The generated components include but are not limited to: software modules and data structures, rules and rule specifications, templates, and various types of media elements (such as video, audio, interactive elements, and media for the sensory impaired).

In one embodiment, program instance compiler 110 is implemented using a web-based model-view-controller (such as the open source web application framework Django™, registered trademark of Django Software Foundation), which defines data structures and access methods for a number of capabilities, including but not limited to: user and social software administration frameworks; program activities and dependencies; activity ranges and constraints (including temporal, spatial, and physical ranges and constraints); relevant information and motivational content; incentives and reward structures via badges; client/server elements and supporting communication protocols for PUSH-style messaging to users; visual display information for individual user and team (social) goal progress (such as progress bars); and various types of information associated with the health/wellness program that are informative, instructional, demonstrative, or other. In an alternative embodiment, program instance compiler 110 includes a web-based Python implementation, which defines data structures and access methods for a goal-setting dialog server that handles multiple simultaneous dialog responses for different named users. In a further embodiment, dialog responses are based on Artificial Intelligence Markup Language (AIML) specification files and executed using PyAIML.

Program instance engine 112 includes a number of interconnected components. In other words, the various components included in program instance engine 112 have the capability to pass information to and from any other component within the engine. In the example shown in FIG. 1, program instance engine 112 includes a presentation management module 114, an interaction management module 116, a social support module 118, a customization module 120, a modified program instances database 122, a contextual data acquisition module 124, a program instances database 126, a program management module 128, a recommendation engine 130, a coaching agent 132, a dialog agent 134, and a number of models (including a user model 136, a goal model 138, a team model 140, and a dialog model 142).

Program instances database 126 stores data about program instances as assembled from program instance compiler 110. Note that in the example shown in FIG. 1, program instances database 126 is part of program instance engine 112. Alternatively, program instances database 126 can also reside externally to, while still being accessible by, program instance engine 112. In some embodiments, program instance engine 112 is deployed in a client-server manner in which the user-focused elements reside on the client and the team or general elements reside on the server. In some embodiments, program instance engine 112 is deployed as a monolithic system. In some embodiments, program instance engine 112 is deployed as a distributed system with each component completely distributed among several computing systems.

Presentation management module 114 is responsible for controlling the information flow to the user through display, sound, haptic feedback, Braille display, or any other available forms of information conveyance to the user. In one embodiment, presentation management module 114 includes an iPhone® (registered trademark of Apple Inc. of Cupertino, Calif.) presentation module that is implemented using a collection of iOS (registered trademark of Apple Inc. of Cupertino, Calif.) view controllers. The iPhone presentation module provides the following capabilities: program activities and dependencies, activity ranges and constraints (including temporal, spatial, and physical ranges and constraints), relevant information and motivational content, incentives and reward structures via badges, visual display information for individual user and team (social) goal progress (such as progress bar), and various types of information associated with the health/wellness program that are informative, instructional, demonstrative, or other.

Interaction management module 116 is responsible for controlling information flow from the user through various input mechanisms, including but not limited to: touch screen, keyboard, controller, voice control, brain-computer interface, or any other available forms of information conveyance from the user. In one embodiment, interaction management module 116 includes an iPhone interaction module that is implemented using a collection of iOS view controllers. The iPhone interaction module facilitates the user to interact with the system with the following information: program activities and dependencies, relevant information and motivational content, incentives and reward structures via badges, visual display information for individual user and team (social) goal progress (such as progress bars), and various types of information associated with the health/wellness program that are informative, instructional, demonstrative, or other.

Social support module 118 provides social support to users in order to increase user stickiness (including adoption, engagement, and completion) with the health/wellness program. The core of this module supports, facilitates, analyzes, and enables contributing to social conversations (text and media). In one embodiment this appears as an activity feed on an iPhone. Social support module 118 include various support mechanisms designed specifically for social teams and personalized coaching agents that can guide, engage, support, motivate, and reward users. In one embodiment, social support module 118 includes an iPhone presentation that is implemented through a collection of iOS view controllers. In a further embodiment, social support module 118 facilitates the creating of shared content, commenting on content created by others, and annotating content created by others (e.g., a "high-five" annotation).

Customization module 120 allows a user to select and customize a health/wellness program by interacting with the program model stored in program model database 106. In addition to selections made by individual users, customization module 120 also facilitates selection and customization of program instances via a method of curation by a social community. All modified program instances are stored as new program instances in modified program instances database 122.

Contextual data acquisition module 124 is responsible for monitoring users' data streams and sensor data (e.g., GPS, mobile location, WiFi connection point, etc.), as well as communicating directly with the users to determine their current context. In one embodiment, contextual data acquisition module 124 also determines the context probability distribution, which is shared with other components in the system in order to provide contextually relevant information/interventions.

Program management module 128 is responsible for administering the program instances by keeping up with task planning, assignment, tracking, re-planning, and off-track mitigation. Program management module 128 also collects statistics across all users for all tasks within the defined programs.

Recommendation engine 130 is responsible for providing advice to users concerning program tasks, including deep recommendation of task activity issues, such as a recommendation of a particular task to be performed. Moreover, recommendation engine 130 may also assist in moving from program to program based on user performance, user models, and program information. For example, recommendation engine 130 may recommend that the user move from the current exercise program to a more rigorous one based on the user's increased strength.

Coaching agent 132 is responsible for providing one-on-one as well as team interactions with regard to task performance and mastery of health habits (e.g., diet and exercise). Coaching interventions are selected to improve user motivation, and specification and adoption of specific behavioral goals and implementation intentions; maximize the achievement of adopted goals and plans; and revise and re-plan goals and implementation intentions in the face of failures or barriers. Interventions are selected based on predicted effectiveness, which can be assessed based on user models and context. Interventions may be delivered over different communication channels, such as text messages, emails, direct dialogs (textual or verbal), calendar reminders, and team discussion boards. The types of interventions may include but are not limited to: informational messages to increase user knowledge relevant to goal achievement, reinforcement, reminders, motivational interviewing, planning dialogs, coping/re-planning dialogs, information visualization, peer help/support elicitation, user education, and other ways that can help users to complete program goals. In one embodiment, coaching agent 132 includes a web-based Python implementation, which defines data structures and access methods for a goal-setting dialog server that handles multiple simultaneous dialog responses for different named users. In a further embodiment, dialog responses are based on Artificial Intelligence Markup Language (AIML) specification files and executed using PyAIML.

Dialog agent 134 is responsible for marshaling conversational data and system data between the users and the various components within program instance engine 112. In one embodiment, dialog agent 134 also performs conversational text analysis including sentiment analysis, and provides the analysis results as data to the system.

The various models, including user model 136, goal model 138, team model 140, and dialog model 142, are used to capture specific user and interaction nuances and modalities in order to make better decisions within the system. In one embodiment, an iOS Core Data implementation defines data structures and access methods for the following model elements: user profile, team profile, goal definitions, user activities with respect to goals, and team activities with respect to goals. In a further embodiment, a web-based Python implementation defines data structures and access methods for a goal-setting dialog server that handles multiple simultaneous dialog responses for different named users. Dialog responses are based on AIML specifications.

Figure 1B:
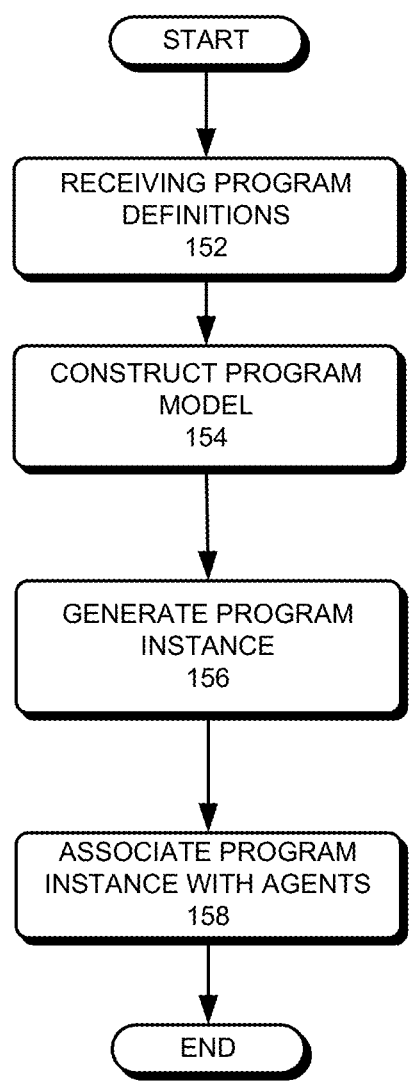
FIG. 1B presents a diagram illustrating an exemplary process of creating a health/wellness program using the generic platform, in accordance with an embodiment of the present invention.

FIG. 1B presents a diagram illustrating an exemplary process of creating a health/wellness program using the generic platform, in accordance with an embodiment of the present invention. During operation, the system receives a set of program definitions (operation 152). The program definitions can be a set of menu items describing the health/wellness program. For example, the definitions of a diet program, such as South Beach Diet (registered trademark of South Beach Diet Trademark Limited Partnership), may include a list of food and the recommended intake amount for each type of food. Similarly, the definitions describing an exercise program may include a list of exercises to be performed. Other information may also be included in the program definitions, such as motivational and instructional material, or reward information associated with each phase of the program. In one embodiment, the generic platform provides an interactive user interface that allows the program creator to define a health/wellness program.

Based on the received program definition, the system constructs a program model (operation 154). In one embodiment, the program model quantifies the program definitions and can be represented in a number of ways, such as a graph model, a data structure, a file structure, etc. Subsequently, the system generates a program instance that enables the execution of the health/wellness program on the generic platform (operation 156). The program instance may include software and data structures, rules and rule specifications, templates, and associated media elements. Note that the program instance is generated based on available generic platform elements. The generated program instance is then associated with various modules (agents) that will be deployed during the execution of the program (operation 158). The modules include but are not limited to: a presentation module, a contextual data acquisition module, a social support module, a recommendation engine, a coaching agent, a dialog agent, etc.

FIG. 2 presents a diagram illustrating the system flow as perceived by the user, in accordance with an embodiment of the present invention. In the example shown in FIG. 2, the system flow includes a number of stages: stages 202, 204, 206, 208, 210, and 212. The direction of the system flow is indicated by the arrow. In FIG. 2, stage 202 is the initial stage where one or more users download the app for the health/wellness program. Note that the health/wellness program may be provided by different organizations, including but not limited to: a healthcare provider, a health insurance provider, a private corporation, a government agency, a health site, and various health/wellness-related brands. Also, note that the user can download the app onto an associated computing device, such as a smartphone or a personal computer.

In stage 204, the user can join a team. In this stage, the user sets a personalized health/wellness goal and finds teams that he is interested in joining. In stage 206, the user picks a program from the available programs that are offered by the various providers. Note that the order of stages 204 and 206 may be reversed.

Subsequent to the user's joining a team and selecting a program, at stage 208 the user executes the program, which may be a diet plan, an exercise plan, or a combination thereof. While executing the plan, users can report their activities (such food consumed or amount of exercise performed) and get nudges from the system and their corresponding social teams for staying on track with the program. The system also tracks individual and team progress.

Stage 210 is the reward stage where the users earn rewards for performing program tasks. In some embodiments, the reward enables the users to visualize their achievements, such as earning badges or points. In some embodiments, the system provides rewards to users based on team success.

Stage 212 is the advance stage where the users move to the next level by selecting a new team and setting a new goal (stage 204).

To increase the stickiness of the users to the health/wellness program, the system provides a number of motivational and supporting mechanisms, including a smart agent mechanism that allows the user to set goals and plan with a coach, a social support mechanism that enables the user to achieve his goals with his friends, and a gamification mechanism that allows the user to track his progress and earn rewards.

Smart Coaching Agent

In order to improve the user stickiness to the health/wellness program, a smart coaching agent is used to assist the users in achieving their behavior-changing goals. In some embodiments, the smart coaching agent relies on artificial intelligence and user modeling to accurately assess individual abilities, knowledge, and motivation with respect to behavior-changing goals. The system also accurately models and predicts the effects of interventions on individual achievement of the behavior-changing goals, and implements algorithms and heuristics that optimize the selection and delivery of interventions to maximize individual achievement.

Consistent with general theories of behavioral change, such as the Theory of Planned Behavior (see, e.g., Ajzen, Icek (1 Dec. 1991). "The theory of planned behavior". Organizational Behavior and Human Decision Processes 50 (2): 179-211), the Trans-theoretical Model (see, e.g., Prochaska, J O; Butterworth, S; Redding, Calif.; Burden, V; Perrin, N; Leo, M; Flaherty-Robb, M; Prochaska, J M. Initial efficacy of MI, TTM tailoring and HRI's with multiple behaviors for employee health promotion. Prev Med 2008 March; 46(3):226-31), or PRIME, in some embodiments, the interventions focus on increasing motivation, implementation, or practice and maintenance of specific behavioral goals, such as "eating a healthy breakfast every day" or "walking 10,000 steps per day." Interventions may be delivered over multiple channels, including but not limited to: point-to-point messaging, posts to team conversations, SMS messages, emails, synthetic voices, and calendar reminders. Interventions may include but are not limited to: dialogs for obtaining user background (such as attitudes, social influences, perceived self-efficacy, activity levels, knowledge, preferences, etc.); instruction and education; motivational interviewing to increase motivation to change; guidance and support in defining implementation intentions and coping; troubleshooting and hints to overcome barriers; reminders and messaging to increase motivation and memory of goals and plans; decomposition of complex goals into subgoals; recommendation of less difficult goals when failing on more difficult ones; providing substituting goals as alternatives when appropriate; and providing situational awareness of relevant challenge circumstances or activities to individuals, to teams, across teams, and across challenges.

In some embodiments, the smart coaching agent includes a representation of challenges and behavioral goals to be mastered by a user; a model of the user that includes abilities, knowledge, and motivation; coaching knowledge that includes techniques for monitoring, shaping, diagnosing, and repairing behaviors; and capabilities for messaging, dialogs, and other forms of intervention. The smart coaching agent further implements a measurement-modeling framework. The measurement-modeling framework supports the optimal selection of coaching interventions in a way that dynamically changes with measurements of user states and state-changes; provides a way of updating the estimates of individual abilities, knowledge, and motivation throughout the coaching process; and provides a way of refining its model parameters from data collected on populations of users working on challenges.

In some embodiments, the measurement approach is an extension of the Rasch family of models having desirable properties of a specific objectivity. Specific aspects of the measurement model are informed by computational cognitive theory regarding the functioning of human memory and human behavioral choice. More specifically, the method assumes that behavioral goals can be assigned one or more parameters ($\delta_1 \ldots \delta_D$) representing their difficulty on D latent dimensions. Users can similarly be represented as having latent abilities ($\theta_1 \ldots \theta_K$), and latent motivations ($u_1 \ldots u_M$). Note that the levels of difficulty, motivation, and ability are inter-comparable and measured on the same dimensions. Based on the multidimensional random coefficient multinomial logit (MRCML) model, the probability of a person performing a specific behavioral goal is:

$$Pr(X = 1; A, B, C, \delta, \theta, u) = \frac{\exp(b\theta + a'\delta + c'u)}{1 + \exp(b\theta + a'\delta + c'u)}, \quad (1)$$

where A, B, and C are all multidimensional vectors.

For the purpose of presentation, here we use a simple representation in which every behavioral goal has a unidimensional difficulty, and a user has a unidimensional ability and motivation, and rewrite Eq. (1) as:

$$Pr(X = 1 | \theta, u, \delta) = \frac{\exp(\theta + u - \delta)}{1 + \exp(\theta + u - \delta)}. \quad (2)$$

Hence, if p=Pr(x=1), then $$\log\left(\frac{p}{1-p}\right) = \theta + u - \delta. \quad (3)$$

The probability of a person engaging in a behavior is improved by interventions that increase the motivation and/or ability of the person. Thus, each intervention can be represented by (for example) an additive "boost," $\tau$, which supplies ability or motivation. The right-hand side of Eq. (3) then becomes: $(\theta+u+\tau)-\delta$. Because each intervention may also have its own difficulty and motivation parameters (such as the time cost to process the intervention and the "receptivity" to attend to the intervention), the right-hand side of Eq. (3) should be rewritten as: $(\theta+u+\tau)-\delta-\delta i+ui$, where $\delta i$ and $ui$ represent the difficulty and motivation to process the intervention, respectively. Note that all dimensions range from negative infinity to positive infinity.

The estimates of these parameters may initially be derived from a number of sources, including theory, best practice of experts, standards derived from studies on populations, empirically through observation of a system or related systems, and crowd sourcing or other collaborative measures.

In one embodiment, a Rasch model is used to relate a person's behavior to an attitude to change and the difficulty of that change. Hence, Eq. (3) is rewritten as:

$$\log\left(\frac{p_{ni}}{1-p_{ni}}\right) = \theta_n - \delta_i, \quad (4)$$

where $p_{ni}$ is the probability of a person n to engage in behavior i, $\theta_n$ is the general attitude level of person n, and $\delta_i$ is the cost (or difficulty) of behavior i.

The expression in Eq. (4) may be generalized in a number of ways by taking into account various aspects of $\theta_n$ and $\delta_i$ that may affect the person's engagement in an activity. For example, for $\theta_n$, other aspects of motivation beyond attitude may also be considered, such as self-efficacy, values, beliefs, and social influences. In addition to motivation, $\theta_n$ may also include ability to change in terms of resources, knowledge, and prerequisites and other dependencies. Note that the motivation/ability variable ($\theta_n$) may be derived through observation, estimation, analysis of historical events including prior motivational actions, and social influences. The cost ($\delta_i$), which generalizes the difficulty level of a change, can include physical difficulty, emotional difficulty, economic cost (including both immediate and opportunity costs), and social cost (such as reputation and stigmatization). In some embodiments, both motivation/ability) ($\theta_n$) and costs ($\delta_i$) can include contextual data relating to change, such as location, time, and environmental conditions. In addition, other models for calculating probabilities based on combinations of features, such as regression, item response theory, and other variation of the Rasch model, can be used.

Among the various aspects of $\theta_n$, social influences on behavioral change can be assessed in a number of ways, including: analysis of connections in a social graph (e.g., friends in a social network, conversations in a communication medium) for occurrence and strength of like, dissimilar or related behaviors; assessments of trust, influence, and reputation; and combining the above with social network measures of size, density, degree, centrality, connectedness, reachability, reciprocity and transitivity, distance, flow, cohesion, and changes in any attribute over time.

Given the Rasch model shown in Eq. (4), one can utilize the model for intervention in a number of ways. For example, if the desired probability for change in behavior is set at a certain level (e.g., 80% compliance), and it is observed that the actual occurrence of the desired behavior is not meeting the desired target, then one may intervene by increasing the motivation and/or the ability level (e.g., providing information or other resources, providing encouragement through personal messaging, providing social awareness such as public messaging, influencing others to influence or help individual n); decreasing the cost to individual n by introducing new behaviors that person n can meet and which may lead to better performance on behavior i such as preparation steps and avoidance or repair measures; decreasing the cost to an individual n by deferring behavior i in favor of a different behavior j with a lower cost; and/or changing the cost of behavior i, such as making an environmental or social change related to that behavior (e.g., if the behavior is healthy snacking in a company break room, then making healthy snacks more economical through subsidies or community involved preparation).

Alternatively, if the desired probability for a behavioral change is set to a certain level and one knows or estimates the motivation/ability level of an individual n, then the system may suggest a behavior i that matches the desired probability, where the matching may be some function that specifies a fit such as a distance measure or threshold with tolerances.

According to the aforementioned modeling assumptions, the two basic ways to intervene in order to help a person stop doing something unhealthy and/or start doing something healthy are to increase the motivation and/or ability of a person to make the change or lower the cost for the change. There are different ways to increase motivation and ability, including but not limited to: motivational messaging, including motivational interviewing techniques and structured dialogs; informational messaging to explain the goals and the tasks; setting implementation intentions, such as the use of preparatory acts to actions; and providing awareness of state, trends, predictions, history, norms, standards, competition, collaboration, and other forms of activities related to and affecting behavioral change.

Each of the coaching responses can be triggered by conditions detected in the model around motivation/ability ($\theta_n$) and cost/difficulty ($\delta_i$). In some embodiments, the system uses a web-based service that keeps track of an ongoing agent-to-speaker dialog state involving some number of speakers. Such a web-based service can be implemented as a server listening for connections on a Transmission Control Protocol (TCP) port in the Python programming language and uses a Python version of the Artificial Intelligence Markup Language. Other implementations are also possible, including but not limited to: web services such as Common Gateway Interface calls, Java Servlets, and RESTful interfaces in a web-application framework, such as Django.

One embodiment of the present invention defines a protocol in which a client wishing to talk to the agent makes a connection and is given or supplies a name or other unique identifier, such as an IP address or a universally unique identifier (UUID). This starts a dialog with that speaker, and an AIML dialog instance is started and saved persistently (i.e., an AIML 'brain'). When a request for the next dialog text exchange is made, the server loads the dialog instance, applies the new text and returns the results to the requester. Results are determined by a set of AIML dialog specifications. AIML implementation is augmented to allow an additional specification, namely to change to a new dialog specification to change topics in the dialog by invoking a different AIML dialog specification for this conversation. This arrangement allows for small and efficient dialog states that can be managed and stored persistently for all speakers and served over one or more server connections.

Figure 3A:
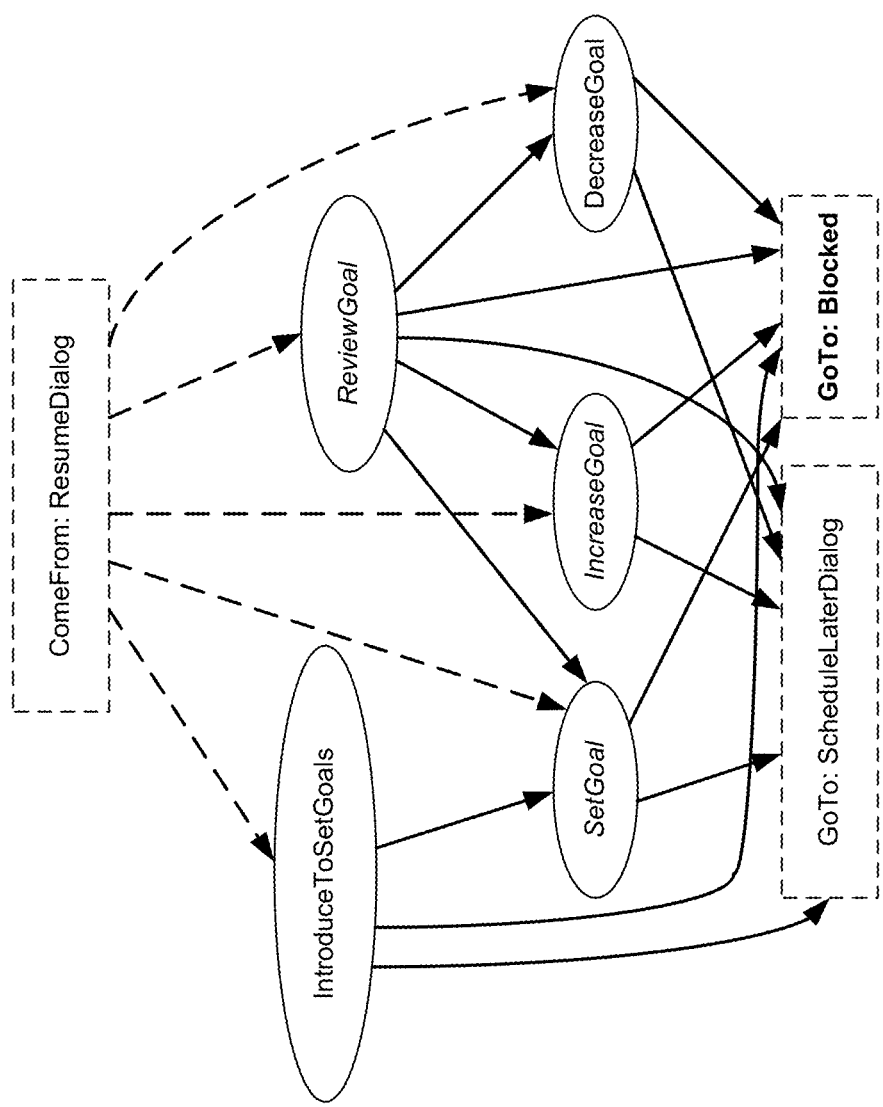
FIG. 3A presents a diagram illustrating an exemplary dialog tree for working with goals, in accordance with an embodiment of the present invention.

FIG. 3A presents a diagram illustrating an exemplary dialog tree for working with goals, in accordance with an embodiment of the present invention. This dialog assumes that a person has just heard about the application but knows nothing about it. This dialog allows a user to set and/or adjust a goal. In FIG. 3A, ovals are dialogs, boxes are dialog support processes, and dashed lines indicate things happening externally to the dialog. In addition, the bold text indicates possible resistance, the italicized text indicates that the node is on path to change, and regular text indicates that the node is a change talk.

Figure 3B:
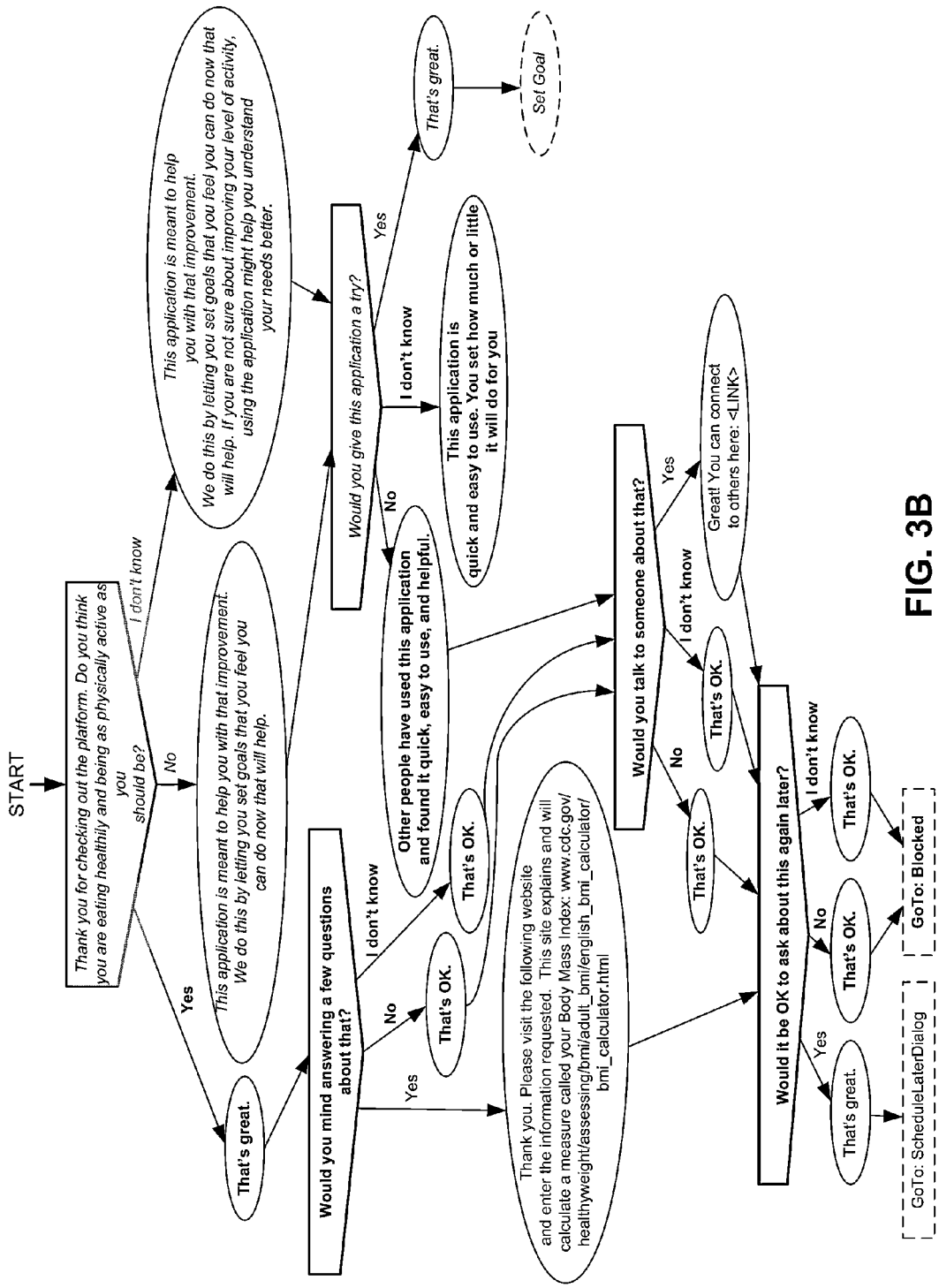
FIG. 3B presents a diagram illustrating an exemplary dialog tree for introducing a person to goals, in accordance with an embodiment of the present invention.

FIG. 3B presents a diagram illustrating an exemplary dialog tree for introducing a person to goals, in accordance with an embodiment of the present invention. Similar to the example shown in FIG. 3A, the dialog in FIG. 3B assumes that the person has just heard about the application but knows nothing about it. More specifically, FIG. 3B shows a conversation between a new user and the smart agent, during which the smart agent elicits feedback from the new user and proceeds based on the user's feedback. Similar to the example shown in FIG. 3A, in FIG. 3B the bold text indicates possible resistance, the italicized text indicates that the node is on a path to change, and regular text indicates that the node is a change talk. Moreover, in FIG. 3B, ovals are "provide" dialogs, pentagons are "elicit" dialogs, boxes are dialog support processes, and anything in a dashed line is an external processes described elsewhere. FIG. 3C presents a diagram illustrating an exemplary AIML dialog specification for the top of the dialog tree shown in FIG. 3B.

In the dialogs shown in FIGS. 3A-3B, a number of techniques are used for motivational conversation structure. For example, in the example shown in FIG. 3B, an elicit-provide-elicit structure for motivational interviewing (MI) is used, shown by alternating reverse houses and ovals. Other MI techniques, such as expressing empathy in the dialog, rolling with resistance (by deferring and revisiting conversational topics as needed), encouraging change talk (by inviting conversations on topics with others), recognizing the autonomy of the speaker (by not setting the agent up as an authority and acknowledging its limitations to speakers as an agent), etc., are also implemented. Moreover, in the examples, the system keeps the focus of conversations within the limits of an automated agent by using simple dialog act schemes, such as restricting to yes/no/maybe response paths.

Smart Recommendation

As described in the previous section, the system includes a recommendation engine that is capable of making recommendations to users concerning program tasks. In some embodiments, the recommendation engine is able to perform meta-level matching that can apply across multiple challenge instances, including matching between users and challenges, matching between teams and challenges, and matching between users and teams.

Figure 4B:
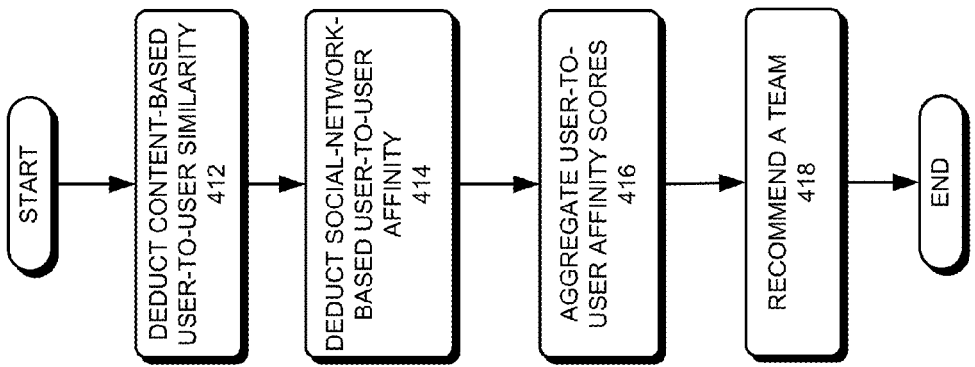
FIG. 4B presents a flowchart illustrating an exemplary user-to-user affinity-based recommendation process for recommending a team to a user, in accordance with an embodiment of the present invention.
Figure 4A:
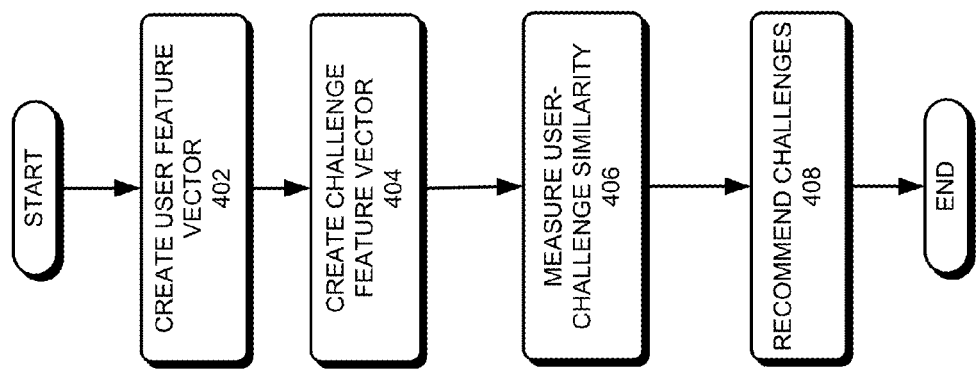
FIG. 4A presents a flowchart illustrating an exemplary content-based recommendation process for recommending a challenge to a user, in accordance with an embodiment of the present invention.

In some embodiments, the recommendation engine recommends a challenge to a user based on user content. This approach requires little data and addresses cold-start problems. FIG. 4A presents a flowchart illustrating an exemplary content-based recommendation process for recommending a challenge to a user, in accordance with an embodiment of the present invention. During operation, the system starts with creating a feature vector for the user (operation 402). The user feature vector may include, but is not limited to: demographic features (such as age, gender, location, etc.); questionnaire responses (such as personality, results of psychological tests, and assessment of interests); and text information, which may include a number of groups of weighted words. The text can be obtained from user profiles (e.g., self-description, goals, etc.); posts, comments, and messages authored by the user within the system; and external text content (user profiles or posts on social media sites, such as Facebook and Twitter). In addition to directly obtained information from the user using profile data or questionnaire responses, the system may also infer user information based on user context collected by a mobile device associated with the user. For example, the user location can be inferred based on GPS data. In addition, the system may also infer user interest based on monitored user activity. In some embodiment, the mobile device or a sensor associated with the mobile device may record the user's activity level (such as speed of running or walking) and biometric data (such as heart rate) and infer the user ability accordingly.

The system also creates a feature vector for the challenge (operation 404). A challenge feature vector may include, but is not limited to: demographic features of current/past participants (such as mean age, gender, location, etc.), mean of questionnaire responses of current/past participants (such as personality, results of psychological tests, and assessment of interests), and text information. The text for the challenge may include the challenge profile (such as title, description, tags/keywords, etc.); user profiles of past/current participants; and posts, comments, messages of past/current participants.

Subsequently, the system measures a similarity between feature vectors of each challenge and individual users based on a number of criteria, including but not limited to: cosine measure, weighted cosine measure, and Pearson correlation (operation 406). Alternatively, the system can measure similarity using the aforementioned same similarity measures on lower-dimensional feature vectors constructed using singular value decomposition. The system then selects a number of top challenges based on the similarity measure and recommends these top challenges to the user (operation 408).

In some embodiments, the recommendation engine recommends a challenge to a user using a collaborative filtering technique. This approach requires a large amount of data, but can reveal patterns that content-based recommendations cannot detect. The filtering may include standard collaborative filtering and sequential, temporal collaborative filtering.

For standard collaborative filtering, the system identifies users who participated in challenge A who also participated in challenge B. The system constructs a user-challenge matrix, where each entry is 1 if a user has participated in the challenge and 0 otherwise. The system then runs any standard collaborative filtering algorithm, such as item-based k nearest neighbors, user-based k nearest neighbors, or singular value decomposition to determine which challenge to recommend to a user.

For sequential, temporal collaborative filtering, the system identifies users who participated in challenge A who participated in challenge B next. The model includes but is not limited to a Markov model with challenges as states. For a Markov model, the system estimates transition probabilities between states (challenges), and recommends challenges to user with the highest transition probability from the most recent challenge.

In some embodiments, the recommendation engine uses a hybrid approach, which combines the outputs from the content-based recommendation and the collaborative filtering (including both the standard filtering and the temporal filtering) recommendation. Various types of aggregation functions can be used to aggregate the recommendation results, including but not limited to: weighted mean of predictions, weighted mean of rank of predictions, and merged top-k predictions. In one embodiment, the system increases the weight of the outputs of the collaborative filtering recommendation as more data is gathered.

In addition to recommending challenges to users, the system also explains to the user why such a recommendation is made. For example, in a case where a 10K running challenge is recommended, if the system makes recommendations based on text content associated with the user, the system may state that, "we recommend the 10K running challenge because it is tagged with 'running' and we saw this word in your profile description;" for collaborative filtering, the system may state that, "we recommend the 10K running challenge because you participated in the marathon running challenge and others who participated in the marathon running challenge also participated in the 10K running challenge;" and for temporal filtering, the system may state that, "we recommend the 10K running challenge because you participated in the 5K running challenge and others who participated in the 5K running challenge also participated in the 10K running challenge next."

Recommending challenges to an existing team is similar to recommending challenges to a user. In fact, it is a group recommendation version of the challenge-user matching. In some embodiments, in order to solve this group recommendation problem, the system defines an aggregate preference function, or social value function, based on individual preferences (or inferred preferences) of the team members. The system may make recommendations based on the mean of the aggregated function (by suggesting challenges that the users like on average), the minimum (or the least misery) of the aggregated function (by suggesting challenges that everyone likes, or doesn't hate, to some degree), or the mean of the top-k users (by suggesting challenges that a subset of k users will like on average). The system may also use a hybrid approach by using a weighted mean of aggregate measures. Depending on the size of the group, the system may adopt one or more recommendation techniques.

To increase the likelihood of a user sticking with the health/wellness program, it is important that the user join a team that can provide essential social support and motivation when needed. In some embodiments, the recommendation engine can recommend a team to a user based on team-level content. Such a content-based recommendation scheme requires no historical data. During operation, the system constructs a feature vector for the user. The user feature vector can be constructed based on text information, which may include a number of groups of weighted words. The text can be obtained from user profiles (e.g., self-description, goals, etc.); posts, comments, and messages authored by the user within the system; and external text content (user profiles or posts on social media sites, such as Facebook and Twitter). The system also constructs a feature vector for the team based on text information associated with the team, such as team name, team description, and team keywords. Subsequently, the system measures similarities between the user and the teams, and recommends top-ranked teams to the user based on the similarity measure.

In some embodiments, the recommendation engine recommends a team to a user based on an aggregation of user-to-user affinity measures. FIG. 4B presents a flowchart illustrating an exemplary user-to-user affinity-based recommendation process for recommending a team to a user, in accordance with an embodiment of the present invention. First, the system deducts content-based user-to-user similarity (operation 412). To do so, the system may construct a feature vector for the respective user, as well as feature vectors for other users on the team, and compute user-to-user similarities between the respective user and each of the other users on the team.

Next, the system deducts social-network-based user-to-user affinity (operation 414). To do so, the system may assign positive scores to users having positive relationships with the respective user. The positive relationship may include direct links (for example, they are teammates of the respective user, they have communicated with the respective user, or they are contacts of the respective user on external sites, such as Facebook), positive interactions (may be indicated by the presence of positive sentiments in previous posts or messages to the respective user), indirect links (such as being a teammate with someone who was a teammate of the respective user, or being a friend of a friend of the respective user on Facebook), and sharing of the same interest (such as having participated in the same challenges with the respective user). On the other hand, the system may assign negative scores to users having negative relationships with the respective user. A negative relationship may be indicated by the presence of negative sentiments in previous messages or posts between a user and the respective user.

Subsequently, the system aggregates individual user-to-user affinity scores obtained from the content-based similarity calculation and the social-network-based affinity calculation (operation 416), and makes a recommendation based on the aggregated result (operation 418). In some embodiments, the system may recommend a team to a user based on the mean user-to-user affinity score between the team and the user. This approach is based on the assumption that the respective user may wish to like people on the team overall. Alternatively, the system may recommend a team for the respective user to join based on the minimum affinity between the respective user and other users on the team. This approach is based on the assumption that the respective user may wish to like everyone on the team at least to a certain degree. The system may also recommend a team based on the average affinity with the top n users on the team, with the assumption that the respective user doesn't have to like everyone on the team, but at least likes a subset of the team with size n.

In some embodiments, the system may recommend a team for the respective user to join based on a team dynamics measure. More specifically, the system first predicts the roles of each user in a team as well as the respective user based on psychological profiling or past team interactions. The predicted roles may include but are not limited to: lurker, emotional supporter, emotional support seeker, information supporter, information seeker, instigator, moderator, etc. An ideal team should have a balanced mix of the different roles. The system then constructs a utility function over the roles of the team members (including the respective user as a team member). The utility function may have the following characteristics: a team with all lurkers will receive a low score; a team with a balanced number of information seekers and information supporters will receive a high score, a team with many instigators but no moderator will receive a low score, etc.

In some embodiments, the system may recommend a team for the respective user to join using a hybrid approach by combining outputs from the content-based recommendation, user-to-user affinity-based recommendation, and the team-dynamics-based recommendation. The aggregated output can be the weighted mean of the three predictions, the weighted mean of ranks of the predictions, the maximum value of the three predictions, or a merged list of the top-k recommendations.

In addition to recommending a team to the respective user, the system also explains why such a recommendation is made. If the team is recommended based on team-level content, the system may state that, "we recommend this team because it is tagged with 'moms' and you have 'mom' in your profile." If the team is recommended based on social-network-based user affinity, the system may state that, "we recommend this team because your friend is on this team," or "we recommend this team because several former teammates of yours are on this team."

Modification and Substitution of Tasks

After a team is formed, the system tracks performance of each individual user, as well as the performance of the team as a whole. When individuals with different capabilities participate in a team activity, there should be a way to equate the performances of the individual team members by taking into account the capabilities of each member. Such a method can be called a handicap system and is often used in games where players at different skill levels compete with or against each other with the handicap providing a scoring compensation to account for the difference in experience and skill. A handicap system broadens the range of participation and competition by allowing individuals with different skill levels to actively participate in the same activity with a means for meaningful scoring for direct comparison of performances.

In some embodiments, when team members who participate in the same program regimens have different personal capabilities, the system scales the individual program tasks in number and/or intensity to provide the same level of difficulty for each participant in the team. Note that making the task difficulty fall within a defined closeness range for all participants on a team provides proper handicapping. These calculations take into account individual performance capabilities and allow the tasks to be adjusted accordingly. Task completion can be reported as completed, partially completed, or not completed. Adding individual contributions to the sum of the team score is performed for each participant by adding the value for each task multiplied by the level of completion, which may follow a function of full credit [1.0], partial credit [0.0, 1.0], or no credit [0.0].

When a user participates in a health/wellness program, either as an individual or as a member of a team, sometimes he may wish to customize the program based on his personal needs and capabilities. For example, a person may participate in a diet program, which requires daily intake of a certain amount of fish. However, this particular individual strongly dislikes fish or lives in a region where fish is not widely available. As a result, the person may want to modify the diet program by substituting the task of eating fish with the task of eating chicken. Similarly, in an exercise program, a user may wish to substitute one type of exercise with a different type of exercise based on his preference or his strength. In general, substitution between tasks needs to take into consideration two aspects. The first is the relative difficulty of each of the tasks with respect to the participant performing and categorical aspects of the task. The second aspect is the main categorical aspect equivalence of the task.

Given a challenge comprised of a set of tasks, with each task t having an associated difficulty d, each difficulty d exists with respect to a participant attribute feature vector, $A(p)=\{a_1, \ldots, a_n\}$, for all participant types such that an A exists for each participant p, with the property that $n_p \geq n_A$ (there are more participants than individual attribute feature vectors, or as many participants as individual attribute feature vectors). Each element a of A represents an attribute relevant to a participant for the task set of a challenge, including but not limited to, aerobic, anaerobic, flexibility, balance, agility, power, upper body strength, lower body strength, stamina, willpower, past values of attributes, and so forth. In the case of food substitutions, nutrition attributes would be used, but may include personal factors similar to exercise substitutions. These values are determined by various methods, including but not limited to: standard instruments of measure (e.g., a set including but not limited to bench press standards, deadlift standards, squat standards, USMC physical fitness test, US Army standards of medical fitness, The President's Challenge Adult Fitness Test, etc.), self-reporting, second- or third-party reporting, historical performance/interaction derived or measured directly, norms (standards) set by individuals, groups, and/or populations, or other means. These attribute values can be assembled into ranges (making classes across the attribute spaces) such that a=(attribute range lower bound, attribute range upper bound). The task difficulty d of a task t for an individual p is determined as the (weighted) normalized sum of all of the attributes with respect to the task:

$$d(t, p) = 1 - \frac{\sum_0^n w(t)_n a_n}{\sum_0^n w(t)_n}, \qquad (5)$$

where $W(t)=\{w_1, w_2, \ldots, w_n\}$ is the weighting vector for task t, and n is the number of attributes. In Eq. (5), it is assumed that all values are normalized in the range [0.0, 1.0]. The higher the value of d, the more difficult the task t is for the participant p. When used, the weighting vector for task t can be set by a number of factors, including but not limited to: important attributes for the task type (e.g., upper body strength is needed for pull-ups); personal preferences; norms (standards) set by individuals, groups, and/or populations; historical performance on the task; and so forth. Weightings can be used to reinforce attributes for task performance with relation to difficulty (e.g., if someone has low upper body strength, then pull-ups would be more difficult for them). Weightings can be determined by experts and are best represented by a function since the weight scales may not be simply linear.

For substitution of an instance x for another instance y, such that a replacement for task $t_x$ for participant $p_x$ with difficulty $d_x$ will be made, a task$_y$ may be chosen such that $|d_y-d_x| \leq \theta$, where $\theta$ is a difficulty-matching threshold. The substitution task$_y$ can be chosen by various methods, including but not limited to: user/group social suggestion, content-based recommendation that matches task and profile descriptions (or other relevant attributes), collaborative filtering of substitutions made by other system participants, heuristic match, taxonomic tree search, etc. The difficulty-matching threshold $\theta$ can be set based on a number of factors, including but not limited to: instructions of the challenge designer, experimentation, group statistical analysis, social norm, self-selection, and group/individual consensus.

Here we present an example that include three tasks; the first task ($t_1$) is running for 1.5 miles, the second task ($t_2$) is swimming for 450 meters, and the third task ($t_3$) is bicycling for 1 mile. The participant attribute vector can be defined as $A(p)=\{a_1=\text{stamina}, a_2=\text{lower body strength}, a_3=\text{upper body strength}\}$. The weights set for the three tasks are: $W(t_1)=\{w_1=1.0, w_2=1.0, w_3=0.5\}$, $W(t_2)=\{w_1=1.0, w_2=0.5, w_3=1.0\}$, and $W(t_3)=\{w_1=0.3, w_2=0.7, w_3=0.2\}$. Hence, for a participant Nancy Drew ($p_1$), whose participant attribute vector is A (Nancy Drew)=$\{0.7, 0.7, 0.3\}$, the difficulties for the three tasks can be calculated as:

$$d(t_1,p_1)=((1.0\times 0.7+1.0\times 0.7+0.5\times 0.3)/2.5)=0.38,$$

$$d(t_2,p_1)=((1.0\times 0.7+0.5\times 0.7+1.0\times 0.3)/2.5)=0.46, \text{ and}$$

$$d(t_3,p_1)=((0.3\times 0.7+0.7\times 0.7+0.2\times 0.3)/1.2)=0.37.$$

Similarly, for a participant Frank Hardy ($p_2$), whose participant attribute vector is A(Frank Hardy)={0.7,0.3,0.7}, the difficulties for the three tasks can be calculated as:

$$d(t_1,p_2)=((1.0\times0.7+1.0\times0.3+0.5\times0.7)/2.5)=0.46,$$

$$d(t_2,p_2)=((1.0\times0.7+0.5\times0.3+1.0\times0.7)/2.5)=0.38, \text{ and}$$

$$d(t_3,p_2)=((0.3\times0.7+0.7\times0.3+0.2\times0.7)/1.2)=0.53.$$

And for a third participant Joe Hardy ($p_3$), whose participant attribute vector is A(Joe Hardy)={0.4,0.3,0.7}, the difficulties for the three tasks can be calculated as:

$$d(t_1,p_3)=((1.0\times0.4+1.0\times0.3+0.5\times0.7)/2.5)=0.58,$$

$$d(t_2,p_3)=((1.0\times0.4+0.5\times0.3+1.0\times0.7)/2.5)=0.50, \text{ and}$$

$$d(t_3,p_3)=((0.3\times0.4+0.7\times0.3+0.2\times0.7)/1.2)=0.61.$$

In this example, Nancy has good stamina and lower body strength, and finds it easier to run or bike, but swimming is more difficult yet reasonably achievable. Frank has poor lower body strength but good upper body strength, and finds swimming easier than running or biking Joe, who is similar to Frank with lower stamina, finds similar results but with higher difficulty for each task overall.

If the difficulty-matching threshold θ were set at 0.05, Nancy could substitute $t_1$ (running) with $t_3$ (bicycling), or vice versa, as either task should provide the same overall challenge for her. Joe could also do the same. However, Frank does not have a suitable replacement task in this task set, because $t_2$ (swimming) is much easier for him and $t_3$ (bicycling) is slightly harder than the allowed threshold for substitution. An outside task would have to be added to the set for substitution consideration for Frank. This method shows the overall difficulty of a task with respect to an individual participant's abilities and allows for a holistic substitution of tasks.

Some tasks may only require consideration of a subset of the individual attributes for substitution, with the focus on the equivalence of those specific attributes with respect to potential substitutions. To do so, one may apply a mask $M=\{m_1, \ldots, m_n\}$, where $m_i \in \{0.0, 1.0\}$ with 0.0 representing exclusion and 1.0 inclusion, to the weight function differences for each task. This way, one can calculate the suitability for substitution based on specific attributes. More specifically, a replacement suitability value r can be calculated as:

$$r(W(t_i), W(t_j), M) = 1 - \frac{\sum_{0}^{n} |w(t_i)_n - w(t_j)_n| m_n}{\sum_{0}^{n} m_n \text{ or } 1.0}, \quad (6)$$

where n is the maximum number of elements. Note that in Eq. (6), the denominator on the right-hand side is set as 1.0 if $\Sigma_0^n m_n \leq 0$.

If we apply a mask M={1.0,0.0,0.0} in the aforementioned example, the replacement suitability between two tasks picked from the three tasks ($t_1$=run 1.5 mile, $t_2$=swim 450 m, $t_3$=bicycle 1 mile) can be calculated as:

$$r(W(t_1),W(t_2),M)=1-(|1.0-1.0|\times1.0/1.0)=1.0,$$

$$r(W(t_1),W(t_3),M)=1-(|1.0-0.3|\times1.0/1.0)=0.3, \text{ and}$$

$$r(W(t_2),W(t_3),M)=1-(|1.0-0.3|\times1.0/1.0)=0.3.$$

Then one can see that since $t_1$ and $t_2$ both require high stamina compared to $t_3$ and the mask isolates for stamina, $t_1$ and $t_2$ are good substitution matches for each other compared with substituting $t_3$ for either $t_1$ or $t_2$.

These substitution techniques (including the non-masked one and the masked one) allow for matching tasks with similar difficulty levels for participants as well as specific attribute requirements for substitution. Both may be required to achieve a well-informed substitution.

User Interface

By using the smart coaching agent that is capable of dynamically delivering interventions based on user feedback or user context, the system can significantly enhance the stickiness of a user to the health/wellness program. In addition to directly nudging individual users to perform tasks toward the desired goals, the smart coaching agent may also indirectly nudge team members to interact with other team members in order to accomplish the team goals. Sometimes, instead of being nudged by the automated agent, a user may respond better if the one nudging him is his team member. Hence, the team aspect is sometimes essential for the success of the health/wellness program. Various techniques can be used to facilitate communications between the smart agent and the user or the team as a whole, and the communication among the team members. In one embodiment, user-to-agent or user-to-teammate communications are enabled by a user interface (UI).

The limited screen size of mobile devices often leads to using multiple separate screens to display information to users. For example, if a user of a health/wellness program wishes to view his personal profile, his progress, as well as the progress of his team members, and messages from the smart coaching agent, he may need to switch between screens because these information may come from different feeds. To facilitate effective information gathering, in some embodiments of the present invention, the generic platform provides a UI that includes a display capable of displaying three distinct sections in a continuous single page view. To view the different sections, the user only needs to swipe up or down to move between view areas.

Figure 5:
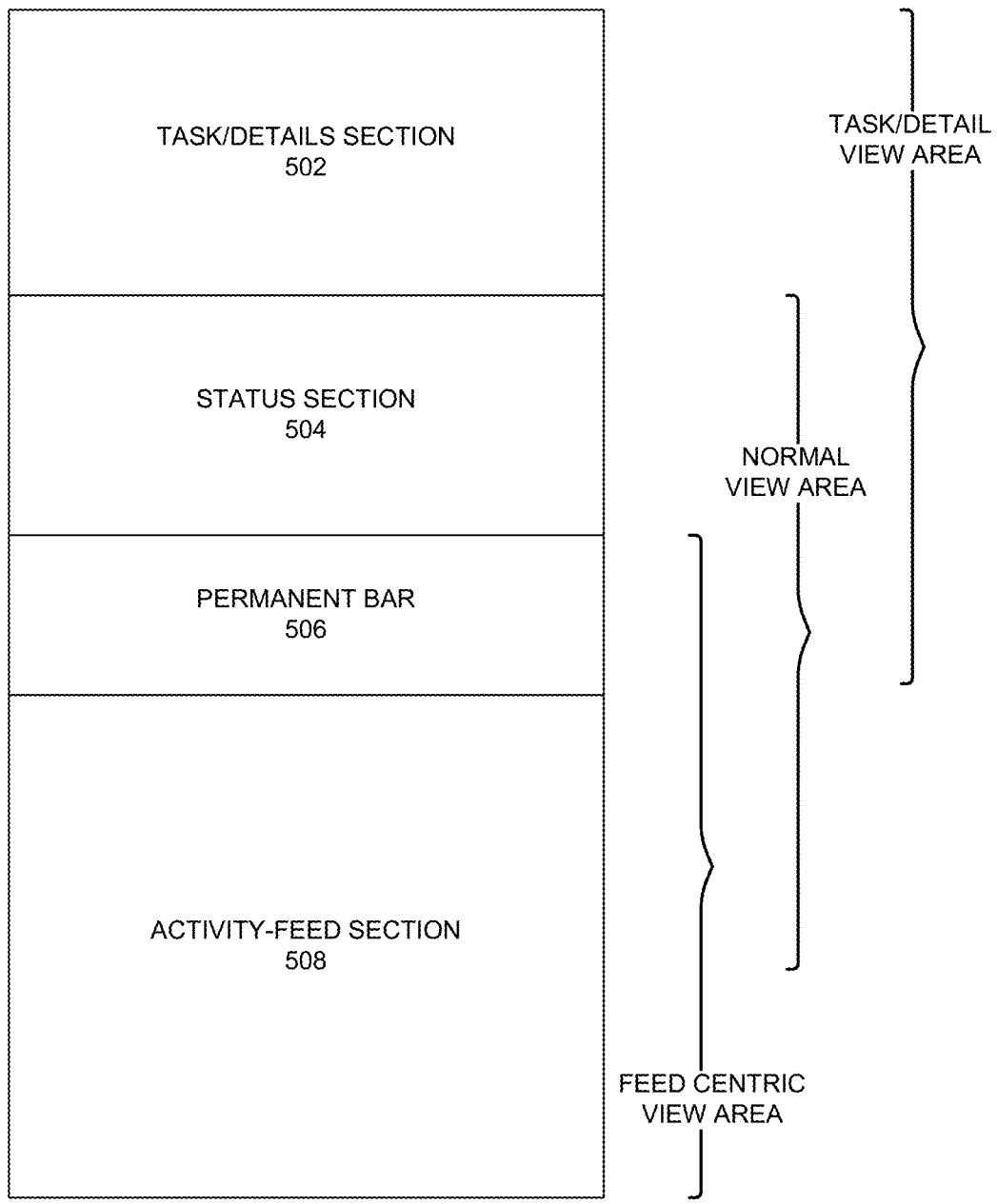
FIG. 5 presents an exemplary overview of the multi-section user interface (UI), in accordance with an embodiment of the present invention.

FIG. 5 presents an exemplary overview of the multi-section user interface (UI), in accordance with an embodiment of the present invention. In FIG. 5, display 500, which can be a touch screen display, includes a task/details section 502 for displaying information associated with a task, a status section 504 for displaying status information of the user, a permanent bar 506, and an activity-feed section 508.

When a user first opens the application, the initial "normal" view typically displays status section 504, permanent bar 506, and at least a portion of activity-feed section 508. Permanent bar 506 typically holds an interaction element that enables the user to make a report or a social media posting.

Activity-feed section 508 presents an activity feed view of data that can extend infinitely. When a user wants to view a detail regarding a task, he can pull down task/details section 502 (which may also be infinitely long) from above status section 504. Note that permanent bar 506 will always appear on the screen as an anchor point. When the user swipes down the screen to view detailed information regarding a task in task/details section 502, permanent bar 506 may become stationed at the bottom of the screen, and information above it, such as information displayed in status section 504 can slide under it and out of view as needed. Similarly, when the user swipes up the screen to view activity feeds (such as posts from team members or the smart agent) in activity feed section 508, permanent bar 506 may become stationed at the top of the screen, and information below it can slide under it and out of view as needed.

Figure 6A:
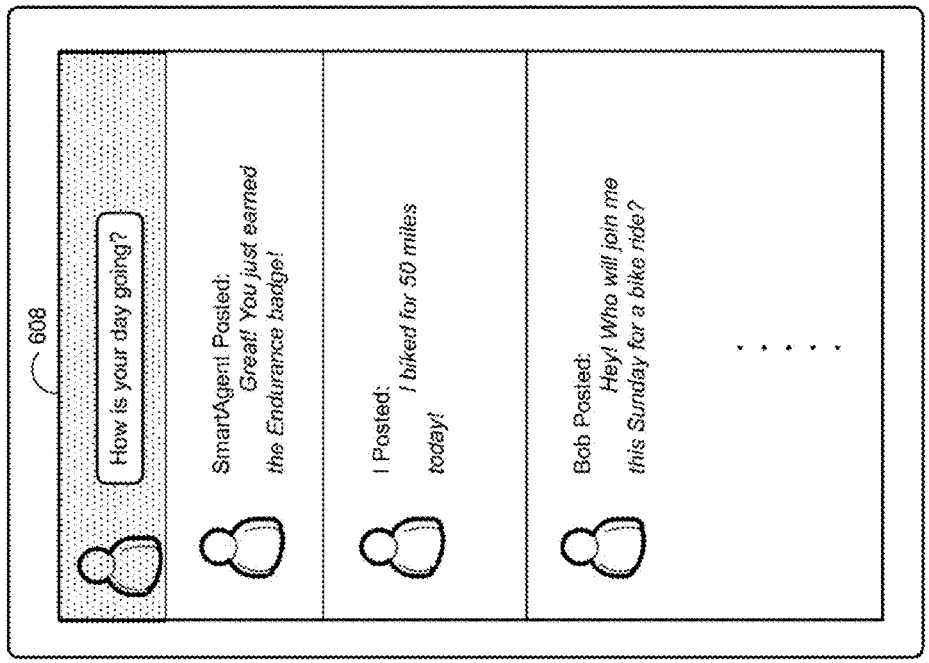
FIG. 6A presents a diagram illustrating an exemplary view of the user interface, in accordance with an embodiment of the present invention.

FIG. 6A presents a diagram illustrating an exemplary view of the user interface, in accordance with an embodiment of the present invention. In FIG. 6A, display 600 includes a task window 602, a personal progress bar 604, a team progress bar 606, and a permanent bar 608.

Task window 602 displays the current challenge in which the user is participating. In the example shown in FIG. 6A, the user is participating in a biking challenge. In one embodiment, the user may tap on the challenge to view details regarding the challenge, such as a daily task. For a biking challenge, the daily task may be riding the bicycle for a certain number of miles. Personal progress bar 604 shows the progress of the user in completing the challenge, and team progress bar 606 indicates the progress made by the team as a whole.

Permanent bar 608 enables interaction between the user and the system. In one embodiment, permanent bar 608 allows the user to talk to the smart coaching agent. In the example shown in FIG. 6A, permanent bar 608 displays a question asked of the user by the smart coaching agent. The user may enter a reply by typing into the input field.

Figure 6B:
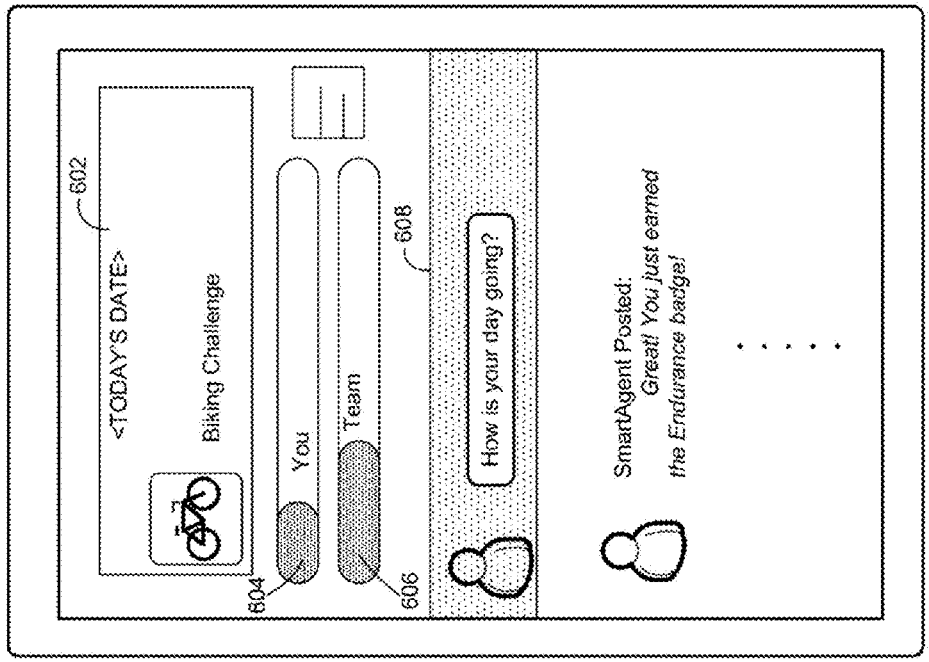
FIG. 6B presents a diagram illustrating an exemplary view of the user interface, in accordance with an embodiment of the present invention.

In FIG. 6A, the region below permanent bar 608 displays various posts to the user, including messages from the smart coaching agent and his team members. To view more posts, the user may swipe up the screen as shown in FIG. 6B. FIG. 6B presents a diagram illustrating an exemplary view of the user interface, in accordance with an embodiment of the present invention. In FIG. 6B, permanent bar 608 now anchors at the top of display 600. The remaining portion of display 600 displays posts from the smart agent, the user himself, and his teammates. The user can continue to swipe up the screen to view more posts with permanent bar 608 remaining on top of display 600.

Figure 6C:
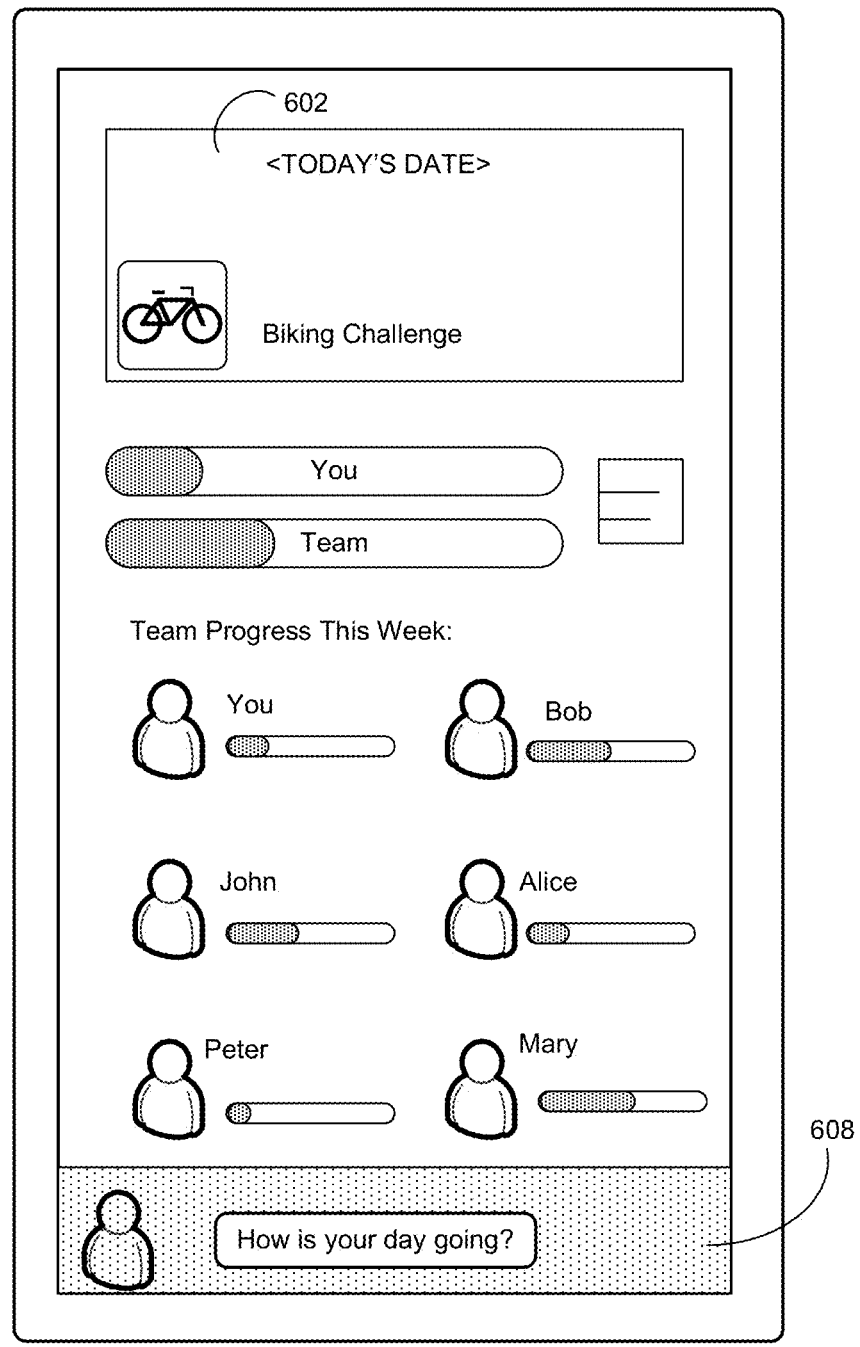
FIG. 6C presents a diagram illustrating an exemplary view of the user interface, in accordance with an embodiment of the present invention.

The user can also view more status details by tapping on the progress bars to reveal more details on the screen as shown in FIG. 6C. FIG. 6C presents a diagram illustrating an exemplary view of the user interface, in accordance with an embodiment of the present invention. In FIG. 6C, permanent bar 608 now anchors at the bottom of display 600. Above permanent bar 608, display 600 displays the progress for the team members of the user. The user can also view more details about a team member by clicking on his name. Permanent bar 608 remains at the bottom of display 600 when more information is displayed above permanent bar 608.

Figure 7:
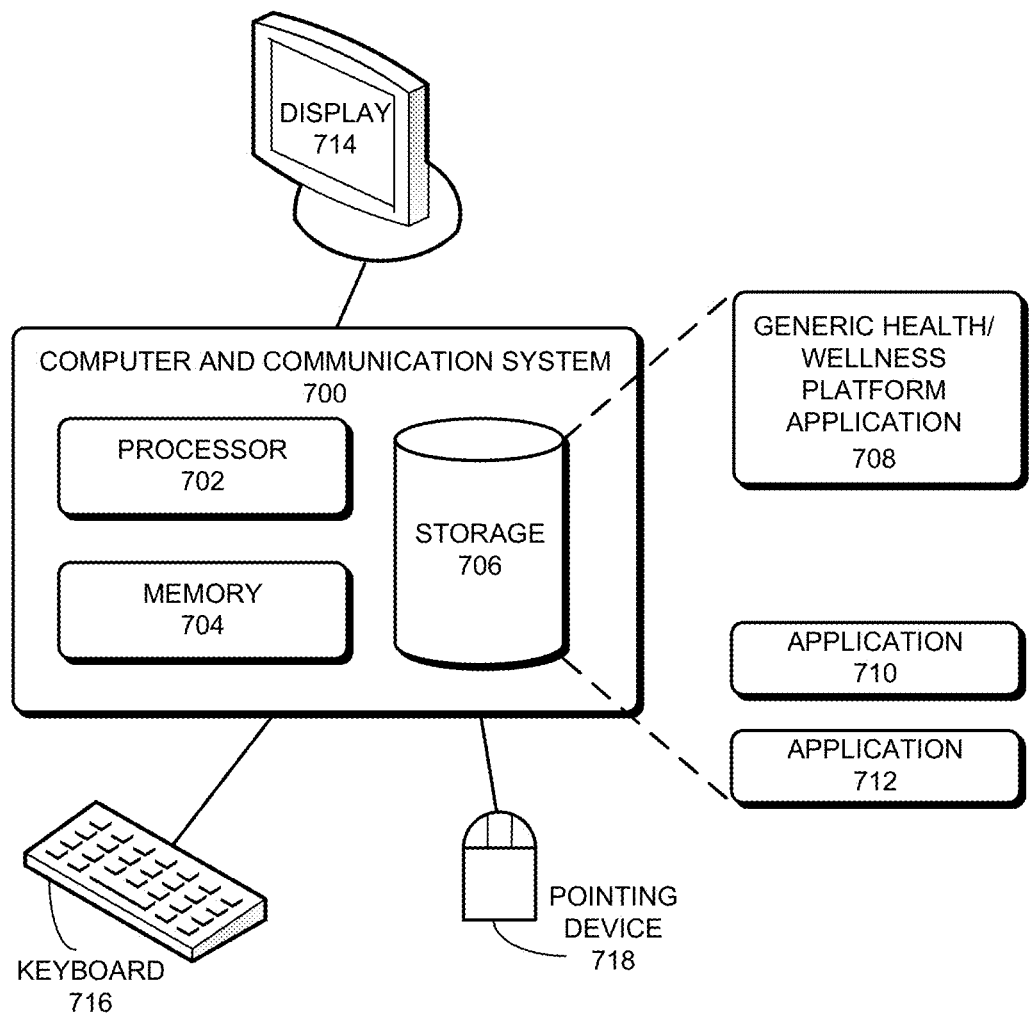
FIG. 7 illustrates an exemplary computer system for a generic health/wellness platform, in accordance with one embodiment of the present invention.

FIG. 7 illustrates an exemplary computer system for a generic health/wellness platform, in accordance with one embodiment of the present invention. In one embodiment, a computer and communication system 700 includes a processor 702, a memory 704, and a storage device 706. Storage device 706 stores a generic health/wellness platform application 708, as well as other applications, such as applications 710 and 712. During operation, generic health/wellness platform application 708 is loaded from storage device 706 into memory 704 and then executed by processor 702. While executing the program, processor 702 performs the aforementioned functions. Computer and communication system 700 is coupled to an optional display 714, keyboard 716, and pointing device 718.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

The foregoing descriptions of various embodiments have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention.

What is claimed is:

1. A computer-executable method for creating a health/wellness program on a generic health/wellness platform, comprising:

presenting to a program creator, by a server executing the generic health/wellness platform, a program editor with an interactive interface;

obtaining, by the server, a set of program elements specified by the program creator via the program editor, wherein the program elements include one or more of: program activities, activity ranges, incentive structures, and reward structures corresponding to the health/wellness program;

compiling, by the server, based on the program elements and a generic platform element library, a computer-executable program instance comprising a set of health/wellness modules, a data structure, and a media element, wherein the modules include a coaching agent executable to:

determine a motivation level and an ability level of a user to achieve a goal defined by the program instance; and estimate, based on the motivation level and ability level, a probability that the user will achieve the goal, wherein the probability increases with the motivation level;

executing, on the server or a client device, the program instance; and in response to the estimated probability being less than a predetermined threshold, delivering, via the program instance, coaching interventions to increase the user's motivation level and probability of achieving the goal.

2. The method of claim 1, wherein the health/wellness modules include one or more of:

a social conversation engine configured to facilitate social support to the user from a teammate or a second user;

a contextual data acquisition module configured to monitor the user's communication or location;
a recommendation engine;
a coaching agent configured to encourage the user's achievement of health goals and plans; and
a dialog agent.

3. The method of claim 2, wherein the health/wellness modules include both a recommendation engine and a contextual data acquisition module, and wherein the recommendation engine is configured to provide recommendations to the user of the health/wellness program based at least on user context obtained by the contextual data acquisition module.

4. The method of claim 2, wherein the recommendation engine is configured to recommend to the user one or more of:
a health/wellness program hosted by the health/wellness generic platform;
a challenge associated with the recommended health/wellness program;
a team to join for participating the recommended health/wellness program; and
a challenge to the team.

5. The method of claim 1, wherein the interventions are delivered to the user or a teammate of the user.

6. The method of claim 2, wherein the health/wellness modules include the dialog agent, and wherein the dialog agent maintains at least one persistent Artificial Intelligence Modeling Language (AIML) dialog instance.

7. The method of claim 1, wherein the delivered interventions include one or more of:
motivational interviewing with the user;
dialogs with the user regarding user attitudes;
decomposition into subgoals; and
troubleshooting barriers of the user.

8. The method of claim 1, wherein the motivation level and ability level of the user are determined based on a model of the user comprising abilities, knowledge, and motivation.

9. The method of claim 1, wherein estimating the probability the user will achieve the goal is based on a measurement-modeling framework:
wherein the measurement-modeling framework implements an optimal selection of coaching interventions based on measurements of user states and state-changes;
wherein the measurement-modeling framework can update the determined motivation level and ability level of the user based on a coaching process; and
wherein the measurement-modeling framework can refine model parameters from data collected from a plurality of users.

10. The method of claim 1, wherein the probability as the increasing function indicates an exponential of the obtained motivation level and ability level according to a multinomial logit (MRCML) model within a Rasch model family.

11. A generic health/wellness system, comprising:
a processor; and
a memory storing instructions that, when executed by the processor, cause the health/wellness system to implement:
a program editor with an interactive interface that obtains a set of program elements specified by a program creator, wherein the program elements include one or more of: program activities, activity ranges, and incentive structures, and reward structures corresponding to a health/wellness program;
a program instance compiler that compiles, based on the program elements and a generic platform element library, a computer-executable program instance comprising a set of health/wellness modules that perform functions of the program instance, a data structure, and a media element, wherein the modules include a coaching agent executable to:
determine a motivation level and an ability level of a user to achieve a goal defined by the program instance; and
estimate, based on the motivation level and ability level, a probability that the user will achieve the goal, wherein the probability increases with the motivation level; and
the set of health/wellness modules, to be deployed by the health/wellness platform, that facilitate execution of the program instance for a user:
wherein, in response to the estimated probability being less than a predetermined threshold, the program instance delivers coaching interventions to increase the user's motivation level and probability of achieving the goal.

12. The generic health/wellness system of claim 11, wherein the health/wellness modules include one or more of:
a social conversation engine configured to facilitate social support to the user from a teammate or a second user;
a contextual data acquisition module configured to monitor the user's communication or location;
a recommendation engine;
a coaching agent configured to encourage the user's achievement of health goals and plans; and
a dialog agent.

13. The generic health/wellness system of claim 12, wherein the health/wellness modules include both a recommendation engine and a contextual data acquisition module, and wherein the recommendation engine is configured to provide recommendations to the user of the health/wellness program based at least on user context obtained by the contextual data acquisition module.

14. The generic health/wellness system of claim 12, wherein the recommendation engine is configured to recommend to the user one or more of:
a health/wellness program hosted by the health/wellness generic platform;
a challenge associated with the recommended health/wellness program;
a team to join for participating the recommended health/wellness program; and
a challenge to the team.

15. The generic health/wellness system of claim 11, wherein the interventions are delivered to the user or a teammate of the user.

16. The generic health/wellness system of claim 12, wherein the health/wellness modules include the dialog agent, and wherein the dialog agent maintains at least one persistent Artificial Intelligence Modeling Language (AIML) dialog instance.

* * * * *